US010646383B2

(12) United States Patent
Rönnberg et al.

(10) Patent No.: US 10,646,383 B2
(45) Date of Patent: May 12, 2020

(54) ABSORBENT PRODUCT COMPRISING COLORED AREAS

(71) Applicant: ESSITY HYGIENE AND HEALTH AKTIEBOLAG, Göteborg (SE)

(72) Inventors: Peter Rönnberg, Göteborg (SE); Philip Blomström, Göteborg (SE)

(73) Assignee: ESSITY HYGIENE AND HEALTH AKTIEBOLAG, Göteborg (SE)

( * ) Notice: Subject to any disclaimer, the term of this patent is extended or adjusted under 35 U.S.C. 154(b) by 0 days.

(21) Appl. No.: 16/466,463

(22) PCT Filed: Dec. 5, 2016

(86) PCT No.: PCT/SE2016/051215
§ 371 (c)(1),
(2) Date: Jun. 4, 2019

(87) PCT Pub. No.: WO2018/106157
PCT Pub. Date: Jun. 14, 2018

(65) Prior Publication Data
US 2019/0350774 A1 Nov. 21, 2019

(51) Int. Cl.
*A61F 13/513* (2006.01)
*A61F 13/512* (2006.01)
(Continued)

(52) U.S. Cl.
CPC ...... *A61F 13/51394* (2013.01); *A61F 13/514* (2013.01); *A61F 13/5123* (2013.01);
(Continued)

(58) Field of Classification Search
CPC ............ A61F 13/51394; A61F 13/5123; A61F 13/514; A61L 15/56
See application file for complete search history.

(56) References Cited

U.S. PATENT DOCUMENTS

2003/0065299 A1* 4/2003 Carlucci ................. A61F 13/42
604/385.01
2003/0114811 A1 6/2003 Christon et al.
(Continued)

FOREIGN PATENT DOCUMENTS

CN 1599584 A 3/2005
CN 102481211 A 5/2012
(Continued)

OTHER PUBLICATIONS

First Chinese Office Action dated Oct. 29, 2019 issued in Chinese patent application No. 201680091306.X (8 pages) and its English-language translation thereof (8 pages).

*Primary Examiner* — Ariana Zimbouski
(74) *Attorney, Agent, or Firm* — Faegre Drinker Biddle & Reath LLP

(57) ABSTRACT

An absorbent product includes a liquid permeable topsheet, a liquid impermeable backsheet, and an absorbent core enclosed between the topsheet and the backsheet. The absorbent core includes an absorbent fibrous layer, a liquid inlet layer, and a carrier layer, in which a transversally central region is arranged in the liquid inlet layer. The central region extends along the entire longitudinal length of the absorbent core, and includes a plurality of slits arranged in a pattern. The slits are in the form of dilated slit openings in a part of said central region, which is comprised in an intermediate portion of the absorbent core, and the slits are in the form of non-dilated slits in parts of said central region, which are comprised in one or both of front and rear portions of the absorbent core.

18 Claims, 5 Drawing Sheets

(51) Int. Cl.
    *A61F 13/514*     (2006.01)
    *A61L 15/56*     (2006.01)
    A61F 13/472     (2006.01)
    A61F 13/538     (2006.01)

(52) U.S. Cl.
    CPC ............ *A61L 15/56* (2013.01); *A61F 13/472* (2013.01); *A61F 13/5126* (2013.01); *A61F 13/538* (2013.01); *A61L 2300/442* (2013.01)

(56) References Cited

U.S. PATENT DOCUMENTS

| | | |
|---|---|---|
| 2010/0036351 A1 | 2/2010 | Larson et al. |
| 2012/0095426 A1 | 4/2012 | Visscher et al. |
| 2014/0295134 A1* | 10/2014 | Wood ................ B01J 20/28054 428/135 |
| 2016/0074237 A1 | 3/2016 | Rosati et al. |
| 2017/0027778 A1 | 2/2017 | Stridfeldt et al. |

FOREIGN PATENT DOCUMENTS

| | | |
|---|---|---|
| CN | 103153250 A | 6/2013 |
| CN | 105101926 A | 11/2015 |
| CN | 105828776 A | 8/2016 |
| WO | WO-2011/025485 A1 | 3/2011 |

\* cited by examiner

ABSORBENT PRODUCT COMPRISING COLORED AREAS

This application is a § 371 National Stage Application of PCT International Application No. PCT/SE2016/051215 filed on Dec. 5, 2016, which is incorporated herein in its entirety.

TECHNICAL FIELD

The present disclosure relates to an absorbent product, such as a sanitary napkin, including a liquid permeable topsheet, a liquid impermeable backsheet, and an absorbent core enclosed there between, and to a method for manufacturing such absorbent products.

BACKGROUND

For absorbent products such as sanitary napkins there are high requirements that they are discreet, soft and comfortable to wear and at the same time have a reliable security against leakage.

For sanitary napkins intended to absorb menstrual fluid being more viscous than urine, it is often more difficult for the body fluid to reach the absorbent core below the top sheet. Menstrual fluid may easily move around on the user facing side of the top sheet under the influence of gravity, motion and pressure by the user. Migration of menstrual fluid to the edges of the product increases the likelihood of leakage, and further smears the menstrual fluid against the skin of the user making cleanup more difficult. It is desirable that products used for absorbing menstrual fluids are able to give the user a feeling of secureness and a visual impression that the menstrual liquid is absorbed by an absorbent core, and to visually emphasize the function of the absorbent product. Further, it is desired to minimize the cost of manufacturing the absorbent products.

SUMMARY

The present disclosure relates to an absorbent product including a liquid permeable topsheet, a liquid impermeable backsheet, and an absorbent core enclosed between the topsheet and the backsheet, said absorbent core having a length extending in a longitudinal direction of the absorbent product, between a front edge and a rear edge, and having longitudinally extending side edges. The absorbent product includes an absorbent fibrous layer arranged on the side of the absorbent core, which is closest to the liquid impermeable backsheet, a liquid inlet layer arranged on the side of the absorbent core, which is closest to the liquid permeable topsheet, and a carrier layer arranged between the liquid inlet layer and the absorbent fibrous layer. A transversally central liquid inlet region is arranged in the liquid inlet layer, extending in the longitudinal direction of the absorbent core and having substantially longitudinally extending side edges, in which region the liquid inlet layer includes a plurality of inlet openings arranged in a pattern, which covers the liquid inlet region. The carrier layer includes one or more colored areas located below the liquid inlet region, and the liquid inlet layer is made of a material having an opacity of 5-60%, or 10-50%, or 10-40%, so that the one or more colored areas are visible through the material of the liquid inlet layer, and the liquid permeable topsheet includes a see-through material, through which the one or more colored areas are visible.

The plurality of inlet openings in the liquid inlet layer may be formed from a plurality of slits, which have been dilated into inlet openings by transversally extending a web of liquid inlet material, from which the liquid inlet layer is made, before incorporation into the product.

The one or more colored areas may be located on a surface of the carrier layer facing the liquid inlet layer or on a surface facing the absorbent fibrous layer. The absorbent core may include a front portion and a rear portion and an intermediate portion located between the front and rear portions, in the longitudinal direction of the absorbent core, and wherein the carrier layer includes one or more colored areas, located in one, two or all of said portions.

The liquid inlet region may extend along the entire longitudinal length of the absorbent core. The liquid inlet layer includes side edge regions, located on either side of the inlet region in the transversal direction of the absorbent product, between the inlet region and the longitudinal side edges, of the absorbent core, and wherein the liquid inlet material in each of said side edge regions is free from openings. The carrier layer may include one or more colored areas, located below said side edge regions.

The one or more colored areas may be applied to the carrier layer by printing. The liquid inlet layer may be made of a liquid inlet polymer foam material or wadding material having a thickness of 0.5-3 mm, or 1-2 mm. The liquid inlet material may suitably be a hydrophobic polymer foam material having open or closed cells. One or more additional colored areas may be printed on a surface of the topsheet. The one or more colored areas comprised in the carrier layer may have different colors or different color intensity, and the one or more additional colored areas printed on a surface of the topsheet have different colors or different color intensity.

The carrier layer may be made of a nonwoven material or tissue material, or a combination thereof.

The present disclosure further relates to a method of manufacturing the absorbent product above, including the steps of cutting a plurality of slits in a central region of a continuous web of liquid inlet material, said slits extending longitudinally in the machine direction; extending the web of liquid inlet layer material transversally in the cross machine direction, whereby the slits are dilated into openings; applying adhesive to a continuous web of carrier material; combining the continuous web of liquid inlet layer material and the web of carrier material into a combined web; cutting liquid inlet layer components from the combined web; providing absorbent components from a continuous web of fibrous absorbent material; enclosing the liquid inlet layer component and absorbent component between a continuous web of topsheet material and a continuous web of backsheet material; joining at least the topsheet material and the backsheet material along the outer edges of the absorbent product; cutting the combined material into a desired shape, thus obtaining the absorbent product; wherein when extending the web of liquid inlet material transversally in the cross machine direction, said web of liquid inlet material is extended to a predetermined desired transversal width M, thereby dilating the slits into openings; and one or more colored area, is present on the web of carrier material before applying adhesive thereto.

The colored areas may be applied to the web of carrier material by printing. Further, the method may include a step of applying one or more colored areas on a surface of the topsheet. The web of liquid inlet material may be a web of polymer foam having open or closed cells.

DETAILED DESCRIPTION OF PARTICULAR EMBODIMENTS

Figure 1A:
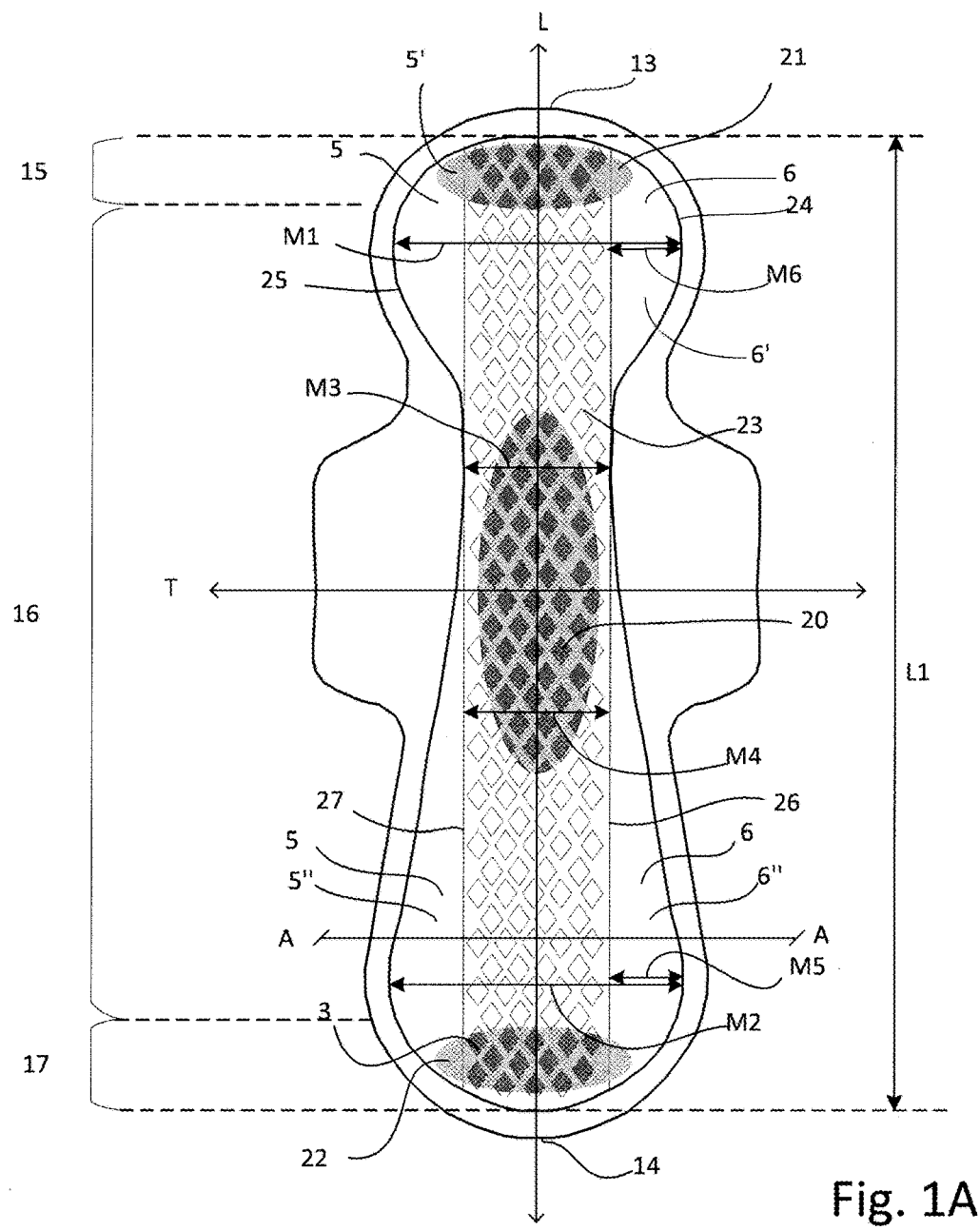
FIG. 1A shows a schematic top view of an absorbent product according to the present disclosure.

The present disclosure relates to a hygiene absorbent product, such as a sanitary napkin, a panty liner, an incontinence shield, or a diaper. The absorbent product includes an absorbent core disposed between a liquid permeable topsheet and a liquid impermeable backsheet. The absorbent product has a transversal rear end edge intended to be orientated rearwards during use of the absorbent article, and a front end edge intended to be facing forwards towards the abdomen of the wearer. The absorbent core includes an absorbent fibrous layer arranged on the side of the absorbent core, which is closest to the liquid impermeable backsheet, and a liquid inlet layer arranged on the side of the absorbent core, which is closest to the liquid permeable topsheet, and a carrier layer arranged between the liquid inlet layer and the absorbent fibrous layer. The liquid inlet layer may be made of foam material or of wadding material. An absorbent product including a foam material is experienced as soft and is also aesthetically pleasing for many users. The continuous structure of many foam materials gives good pliability and an ability to spring back and to substantially return to its original form after having been exposed to outer loading, which contributes to the wearer comfort. The absorbent core extends in a longitudinal direction between a front edge and a rear edge, and has substantially longitudinally extending side edges, and includes a front end portion, a rear end portion, and an intermediate portion located between the front and rear portions in the longitudinal direction of the absorbent core. A wadding is a fibrous and soft material, which can also provide wearing comfort for the user, when used in the liquid inlet layer. The liquid inlet layer will typically cover the entire absorbent fibrous layer.

The absorbent core includes a transversally central liquid inlet region, which extends in the longitudinal direction of the absorbent core and has substantially longitudinally extending side edges. The central liquid inlet region provided in the liquid inlet layer may be located substantially parallel to a longitudinal center line in the longitudinal direction of the absorbent product, and need not follow the outer contour of the absorbent core or the absorbent product, and it may have substantially the same width over its entire length. In the liquid inlet region, the liquid inlet layer is provided with a plurality of inlet openings arranged in a pattern, such that the pattern covers the area of the liquid inlet region.

The carrier layer arranged below the liquid inlet layer includes one or more colored areas located below the liquid inlet region. The liquid inlet layer is made of a material having an opacity of 5-60%, or 10-50%, or 10-40% (according to ISO 2471:2008 (E)—Paper and board—Determination of opacity (paper backing)—Diffuse reflectance method), allowing the colored areas to be visible through the liquid inlet layer material. Further, the liquid permeable topsheet includes a see-through material, through which the colored areas are visible. This means that the colored areas are visible, or at least can be discerned, from the body facing side of the product. The colored area below the liquid inlet layer visualizes the openings provided therein more clearly, so that they will be more easily recognized by the user. The colored areas may be located in various positions on the carrier layer, and can for example serve to emphasize the function of a particular part of the absorbent product, facilitate orientation or positioning of the product during use. The colored area may have a shape and size such that it extends over the area of the transversally central liquid inlet region and outside thereof. In an embodiment, the material of the liquid inlet layer is not fully transparent, so that the color of the colored area, in areas which are covered by the liquid inlet layer material are somewhat obscured due to the opacity of the material, whereas it appears to be more intense in areas where openings are located in the liquid inlet layer. Materials suitable for the liquid inlet layer may typically have a light or whitish color, which means that the incident will be partially reflected by the material and a colored area located below the material will appear to have a lighter color. Thereby, the colored areas will appear in two color intensities, which contribute to giving a sense of three-dimensionality in the product.

The colored areas may be located on the surface of the carrier layer facing the liquid inlet layer, or on the surface facing the absorbent fibrous layer. When the colored areas are located on the surface facing the absorbent fibrous layer, the carrier layer needs to have a sufficiently low opacity, allowing the colored areas to be visible though the carrier layer. When the colored areas are located on the surface facing the liquid inlet layer, the carrier layer can be made of any suitable material without consideration of opacity. The colored areas may be applied to the carrier layer by printing.

The absorbent core may include a front portion and a rear portion and an intermediate portion located between the front and rear portions in the longitudinal direction of the absorbent core, and wherein the carrier layer may then include colored areas located in one, two or all of these portions. For example, the transversally central longitudinal liquid inlet region may have a main liquid inlet area located within the intermediate portion of the absorbent core. A colored area positioned on the carrier layer within the intermediate portion of the absorbent core emphasizes the function of the inlet area, and gives a three-dimensional impression to it.

The liquid inlet region may extend along the entire longitudinal length of the absorbent core, and colored areas can be located near the front and/or rear end of the core, and can serve to indicate how the absorbent product is intended to be oriented during use.

The plurality of inlet openings in the liquid inlet layer may conveniently be formed from a plurality of longitudinally extending slits, which have been dilated into openings by transversally extending a web of liquid inlet material from which the liquid inlet layer is made, before incorporation into the product, or may be obtained by punching/perforating. Forming the plurality of slits by slitting and extending the inlet layer material has the advantage that no material is cut out from the web, which saves money due to less waste of material, and also improves the handling in the production process by avoiding having a lot of small pieces cut out from the material that may contaminate both the process equipment and the final product. Both wadding and foam materials can be provided with openings in this way. Foam materials have the advantage of being easy to cut and extend, achieving a clean and smooth extended layer, without causing any substantial amount of dust.

Due to the lateral extension of the material, the openings formed by slitting and extending the inlet foam material will be widest at their longitudinal center. When the slit is cut as a straight line in the longitudinal direction of the product, the opening will have a diamond shape. The openings can also have other shapes, which can be obtained by cutting slits having a curved shape, e.g. forms as a wave. The openings formed by slitting and extending the inlet layer material may have a maximum transversal opening width of 1.5-15 mm, or 1.5-5.0 mm, in order to obtain effective liquid inlet in the liquid receiving area. The longitudinal slit length may be 3.0-20.0 mm, 4.0-15.0 mm or 5.0-12.0 mm. For sanitary napkins intended to absorb menstrual fluid being more viscous than urine, it is often more difficult for the body fluid to reach the absorbent core than for absorbent products intended for urine. Menstrual fluid may easily move around on the user facing side of the top sheet under the influence of gravity, motion and pressure by the user. Migration of menstrual fluid to the edges of the product increases the likelihood of leakage, and further smears the menstrual fluid against the skin of the user making cleanup more difficult. By having a slit length of 5-12 mm, menstrual fluid will reach the absorbent core more easily. The longitudinal length of the dilated openings may differ from the slit length, due to the transversal extension of the material, which can decrease the longitudinal length somewhat as the slit are formed into dilated openings. The dilated inlet slit openings may have a width in a transversal direction of the absorbent core which is 30-100% of their length in the longitudinal direction of the absorbent core, in order to be large enough to effectively letting through liquid into the absorbent layer.

The openings may have a longer dimension in the longitudinal direction of the absorbent product than in the transversal direction, thus giving the opening a generally oval shape the longitudinal direction, which gives the user a visual impression of good liquid wicking in the longitudinal direction. The plurality of openings creates a pattern of the openings in the liquid inlet material. The slits may be provided in staggered rows extending in the longitudinal direction, where the slits in each longitudinal row of slits have a longitudinal length, and are located at a slit distance between adjacent end points of two sequential slits in the row, and the longitudinal rows are staggered such that adjacent rows are offset by 50% in the longitudinal direction, with a row distance between two adjacent rows. The distance between adjacent inlet openings in liquid inlet region may be 1.0 to 9.0 mm. A short distance between the openings improves the inlet rate. The liquid inlet layer material may alternatively have other slit patterns, or combinations of different slit pattern. Such slit patterns of the openings may be formed by providing slits with different lengths, or by having slits with different slit distance between the slits. Also, irregular patterns may be used. The total open area formed by the slit openings in the horizontal plane of the liquid inlet layer material in the central region may be 30-80% of the total area in the horizontal plane of the liquid inlet layer material in the central region, in order to efficiently let liquid through and at the same time provide sufficient stability.

The liquid inlet layer may further include side edge regions located on either side of the central region in the transversal direction of the absorbent product, between the central region and the longitudinal side edges of the absorbent core. In these side edge regions, the liquid inlet material is free from slits, and can also provide softening of the edges of the absorbent core. When a liquid inlet foam material is used for the liquid inlet layer, these side edge regions can function as leakage barriers, as a foam as such does typically not absorb liquid to any substantial extent. The side edge regions have a smooth surface against the user's skin, due to the absence of openings in the foam. Each side edge region of the front and rear portions may have a maximum transversal width of 5.0-50.0 mm, 20-50 mm, or 5.0-20.0 mm. The colored areas present on the carrier layer may be located below the transversally central liquid inlet region and may extend transversally towards the side edges of the absorbent core. Further, additional colored areas may be provided, which are located below the side edge regions and not below the central liquid inlet region.

The absorbent core may have straight and substantially parallel longitudinal side edges. Alternatively, the absorbent core may be curved so as to attain a shape by means of which it includes a front part and a rear part, and an intermediate part, where the transversal width of the intermediate part is smaller than the transversal width of the front and rear parts, thus giving the absorbent core an hourglass shape. By providing an intermediate portion having a narrower width than the front and rear portions, the configuration of the absorbent core, and of the absorbent product, can be better adapted to anatomy of the user's body. The crotch part is a portion which is intended to be placed against the crotch of a wearer during use of the product and to constitute the main acquisition area for body fluid that reaches the absorbent product. The outer contour of the absorbent fibrous layer and the liquid inlet layer need not be the same, thus an hour-glass shaped absorbent fibrous layer can be combined with a liquid inlet layer having straight parallel longitudinal side edges. The width and length of the absorbent core referred to in this disclosure are the dimensions of the combined layers of the core, unless otherwise indicated.

In the part of the central region which functions as a liquid inlet region, i.e. where the slits in the liquid inlet layer are dilated slit openings, the central region may have a maximum transversal width, which is equal to or smaller than the minimum width of the absorbent fibrous layer. The liquid inlet region is thus typically not wider than the absorbent core, thus ensuring that any portion of the liquid inlet region is located where a part of the fibrous absorbent layer is present. If the transversal width of the central region is smaller than the minimum width of the absorbent fibrous layer side edge regions are formed along the entire longitudinal length on each side of the absorbent core.

A transversal width of the liquid inlet region which is equal to the minimum transversal width of the absorbent core means that the liquid inlet region covers as much of the area as possible in the transversal direction, and if the absorbent core has an hourglass shape, no side edges are formed at the location of the minimum transversal width of the absorbent core. This minimizes the amount of liquid inlet layer material needed for manufacture of the absorbent product, since the material from which the liquid inlet layer is made is extended until the liquid inlet region has the same width as the absorbent fibrous layer in its narrowest portion. In this case, front and rear side edge regions, which are free from slits, are formed transversally outside of the central region, in the front and rear part of the absorbent core.

The liquid inlet region may extend longitudinally along 50-100% of the longitudinal length of the absorbent core, in order to allow enough area for effective liquid inlet into the absorbent product. A longitudinal extension of the liquid inlet region of 80-100%, allows effective liquid inlet also when the product is not optimally positioned by the user, and a longitudinal extension of 100% allows for easier manufacture, in addition to the previously mentioned effects, since the liquid inlet region can be provided along an entire longitudinal length of a continuous foam web during manufacture.

The liquid inlet layer may be made of a liquid inlet polymer foam material or wadding material having a thickness of 0.5-3 mm, or 1-2 mm, where the thickness is measured with an applied pressure of 0.5 kPa on a non-apertured and non-stretched piece of said material, as describe below, order to provide wearer comfort and discretion.

The liquid inlet material may be a hydrophobic or hydrophilic foam. In particular embodiments, the liquid material is a hydrophobic polymer foam material having open or closed cells. Hydrophobic foam materials give hydrophobic edge regions, which can function as liquid barriers and will decrease the risk for edge leakage. The plurality of openings present in the central liquid inlet region ensures that the liquid reaches the absorbent layer of the core below the liquid inlet foam layer, even though the foam material is in itself hydrophobic. Also, hydrophobic foam material close to the user's skin may be preferred from a skin care view, since a hydrophobic and dry surface may decrease the risk for bacterial growth and skin irritations.

The foam material may have an open cell structure or a closed cell structure. Foam materials used as liquid inlet layer in absorbent products are often open cell foams, so that liquid can easily enter the foam and consequently also the absorbent core below. However, due to the presence of the plurality of openings in the liquid inlet region, also closed cell foams can be used. In closed cell foams, the liquid will not so easily enter the foam structure itself, and therefore the foam material as such will be kept in a more dry condition, as compared to an open cell foam material, where the pores are connected with each other. The average pore size of the liquid inlet foam material may be greater than the average pore size of the absorbent fibrous layer arranged below the foam, resulting in a pore size gradient and a capillary suction force in the direction from the foam material towards the absorbent fibrous layer below the liquid inlet foam material.

The foam's pliability and flexibility reduces the risk of scrapes. Liquid inlet layers of air laid, cellulose-based layers and liquid inlet layers of non-woven material do not have the same ability to reduce the negative effect of the stiff edges that a stiff cellulose-based absorption layer causes. Flexible foam materials may spring back and return to substantially their original shape after having been exposed to outer loading, and are also pliable. Flexible foam materials also have a padding effect such that the foam material lines the stiff edges and creates a soft distancing element between the user's skin and the stiff edges of the absorbent fibrous layer. The softness and flexibility of a foam material may be of use for example in a premature baby diaper.

Examples of usable foams are polyolefin based foam, polystyrene based foam, PVC foam, polyvinyl alcohol foam, acrylate foam, polyurethane foam, epoxy foam, latex foam, urea-formaldehyde foam, melamine-formaldehyde foam, silicone foam, viscose foam, carboxymethyl cellulose (CMC foam, starch form, chitosan foam, alginate foam, polyactide foam, polyglycolide foam and polycaprolactone foam.

As indicated above, the liquid inlet layer can alternatively be made of a wadding material. Also wadding can be provided with openings by cutting slits and extending the material layer. A wadding is a nonwoven material and may be substantially free from absorbing fibres and superabsorbent material. The nonwoven material of the wadding may comprise thermoplastic polymer fibres, and may be selected from but not limited to, polyesters, polyamides and polyolefins such as polyethylenes (PE) and polypropylenes (PP), and may be a mixture of any of these. The ADL may be of a spunbonded material and may be a spunbond-meltbond-spunbond (SMS) material. The non-woven material may be hydrophilic. A hydrophilic material may be obtained by adding a surfactant.

In particular embodiments, the wadding is a "high loft" wadding material, which refers to low density bulky fabrics, as compared to flat, paper-like fabrics. High loft webs are characterized by a relatively low density. This means that there is a relatively high amount of void space between the fibers. The high loft nonwoven fibrous layer of the invention may typically have a density below 0.200 g/cc, in particular ranging from 0.015 g/cc to 0.150 g/cc, in particular from 0.030 g/cc to 0.100 g/cc, for example 0.065 g/cc. The density can be calculated by dividing the basis weight of the high loft layer by its thickness measured at a pressure of 4.14 kPa (see the method details further below in the Example section).

The high loft nonwoven layer may advantageously be a spunmelt nonwoven. Spunmelt is a generic term describing the manufacturing of nonwoven webs directly from thermoplastic polymers. It encompasses 2 processes and the combination of both: spunlaid (also known as spunbond) nonwoven and meltblown nonwoven. In a spunlaid process, polymer granules are melted and molten polymer is extruded through spinnerets. The continuous filaments are cooled and deposited on to a conveyor to form a uniform web. Some remaining temperature can cause filaments to adhere to one another, but this cannot be regarded as the principal method of bonding. The spunlaid process has the advantage of giving nonwovens greater strength, but raw material flexibility is more restricted. Co-extrusion of second components is used in several spunlaid processes, usually to provide extra properties or bonding capabilities. In melt-blown web formation, low viscosity polymers are extruded into a high velocity airstream on leaving the spinneret. This scatters the melt, solidifies it and breaks it up into a fibrous web.

The high loft nonwoven layer may in particular have a thickness ranging from 0.30 mm to 2.00 mm, for example 1.0 mm as measured at a pressure of 4.14 kPa (according to the test method described further below). The basis weight of the high loft central layer may for example range from 15 gsm to 500 gsm, in particular from 30 gsm to 200 gsm, for example 64 gsm.

The liquid inlet layer may be held in place by adhesive attachment to any adjacent component, for example the absorbent fibrous layer or the topsheet. The absorbent product may also include a carrier layer arranged between the liquid inlet layer and the absorbent fibrous layer.

The liquid inlet layer material may be laminated to the carrier layer material in its extended condition so that the liquid inlet material is fixed to the carrier material with openings in their extended condition. The absorbent product can include an adhesive layer arranged between the liquid inlet layer and the carrier layer, which covers at least an area corresponding to the liquid inlet region, and suitably covers the entire area of the carrier layer, to ensure that the openings within the liquid inlet region are held in a desired position. A suitable construction adhesive is "Adhesive Hotmelt", for example, from Henkel Adhesives, HB Fuller or Bostik. A suitable elastic adhesive is Dispomelt 723U from Henkel Adhesives.

The opacity of materials used for the liquid inlet layer can be influenced by a number of factors. Properties such as porosity, basis weight, density, and thickness affect the opacity due to scattering and absorption of light in the material. Also, the composition of the liquid inlet material can affect the opacity, and the presence of light absorbing/reflecting materials such as pigments or dyes. In the context of the present disclosure, pigments are preferably not included in a liquid inlet foam material, or added only in a small amount. Waddings and foam materials having various degrees of opacity are commercially available.

The liquid inlet layer material has an opacity of 5-60%, or 10-50%, or 10-40% (according to ISO 2471:2008 (E)—Paper and board—Determination of opacity (paper backing)—Diffuse reflectance method) so as to allow colored areas located below liquid inlet layer to be visible from the body facing side of the absorbent core, through the liquid inlet material layer, and at the same time the color of the colored areas is somewhat obscured, in order for the color seen through the openings to be different from the color seen through the material.

If the liquid inlet layer is made of a material having high opacity, i.e. close to 100%, a colored area below the liquid inlet layer material will not be visible through the layer, but only through the openings provided in it.

The opacity is measured according to International Standard ISO 2471:2008 (E)—Paper and board—Determination of opacity (paper backing)—Diffuse reflectance method. The method originates from the paper industry, but it is suitable also in this context. The measuring of the opacity includes the steps of carefully separating the inlet layer from the absorbent product; and measuring opacity on an area that is free from slits or apertures. In case the opacity varies over the area of the inlet layer (e.g. due to partial coloration or differences in basis weight, the least opaque area should be considered representative for the inlet layer. The opacity can be defined as:

Opacity N=100×(1−intensity of the transmitted light/intensity of emitted light)

The carrier layer is liquid permeable and can be made of a nonwoven material, such as airlaid or meltblown or spunbond synthetic fibre nonwoven material, or tissue material, e.g. comprising cellulose fibres, or combinations thereof. When colored areas are present on the garment facing surface of the carrier layer, it can be made of a material having low opacity, such as nonwoven material with low basis weight, e.g. 8-20 g/m$^2$, and opacity of 15-25%, for example nonwoven spunbond from Union with basis weight 16 g/m$^2$ and opacity 15%, or S-Tex nonwoven from Fitesa with basis weight 20 g/m$^2$ and opacity 24%.

The color of the colored areas present on the carrier layer is selected so that the colored areas are visible, or can at least be discerned, from the body facing side of the absorbent product. The liquid-permeable top sheet layer is arranged on a body facing surface of the product and is intended to be in contact with the wearer's skin during use. As said above, in particular embodiments, the liquid inlet foam material is preferably free from, or contains a very low amount of added pigments, and thus has its original whitish color. This allows a wider range of colors to be used for the colored areas on the carrier layer, and improves the effect of the colored areas. The color hue and color density is selected taking the opacity of the liquid inlet layer material and the topsheet material into consideration, in order to obtain the desired visual impression in the absorbent product.

Additional colored areas may be provided on a surface of the topsheet, which may preferably be printed on the surface of the topsheet facing the liquid inlet layer of the absorbent core. The additional colored areas provided on the topsheet, can be located on top of the colored areas provided on the carrier layer, so that the at least partially overlap. Alternatively, the colored areas provided on the topsheet can be located in separate positions, such as longitudinally outward of the colored areas provided on the carrier layer in the front and/or rear end of the absorbent core, and/or transversally outward of the colored area located in the intermediate portion of the absorbent core. Colored areas on the topsheet can be made to appear very distinct since they are not obscured by any layer other than possibly the low opacity top sheet. They can be used for example when it is desired to visualize certain parts or functions in the product by means of continuous distinct lines. Continuous distinct lines can for example be provided along the edges of the product to, longitudinally and transversally in order to visualize an imaginary barrier.

The color of the additional colored areas provided on the topsheet may be the same or different from the color of colored areas provided on the carrier layer. The one or more colored areas comprised in the carrier layer may have different colors or different color intensity, in relation to each other in order to emphasize and visualize certain functions in the product. Also the one or more additional colored areas printed on a surface of the topsheet may have different colors or different color intensity in relation to each other in order, and in relation to the colored areas on the carrier layer.

For example, the colored areas on the carrier layer may be green or blue in parts which become wet during use, e.g. the liquid receiving region, and may have pink or red tones in portions located at the front or rear end of the product to denote the front or rear part of the product. The colored areas on the topsheet may have the same colors as the colored areas on the carrier layer but with a different intensity, or may be different. For example, purple areas or lines can be used to illustrate barriers. By selecting different colors and/or color intensities, function areas such as liquid inlet area and absorption zone, and front, rear and side barriers can be visualized. Indications as to how to position the product during use can be provided for example by a colored area having a certain shape, e.g. a heart shape.

The colors of the colored areas provided on the carrier layer and the topsheet can be expressed in accordance with the CIELAB Color Scale, which is a color space specified by the International Commission on Illumination. It describes all the colors visible to the human eye and was created to serve as a device-independent model to be used as a reference (cf. CIE Publication 15.2 (1986), Section 4.2).

Figure 5:
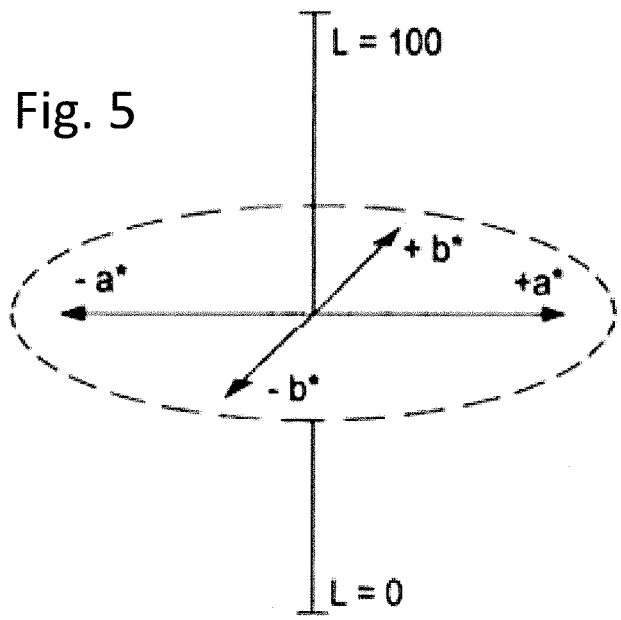
FIG. 5 shows the color "sphere" used for the representation of color in the CIELAB system.
Figure 6:
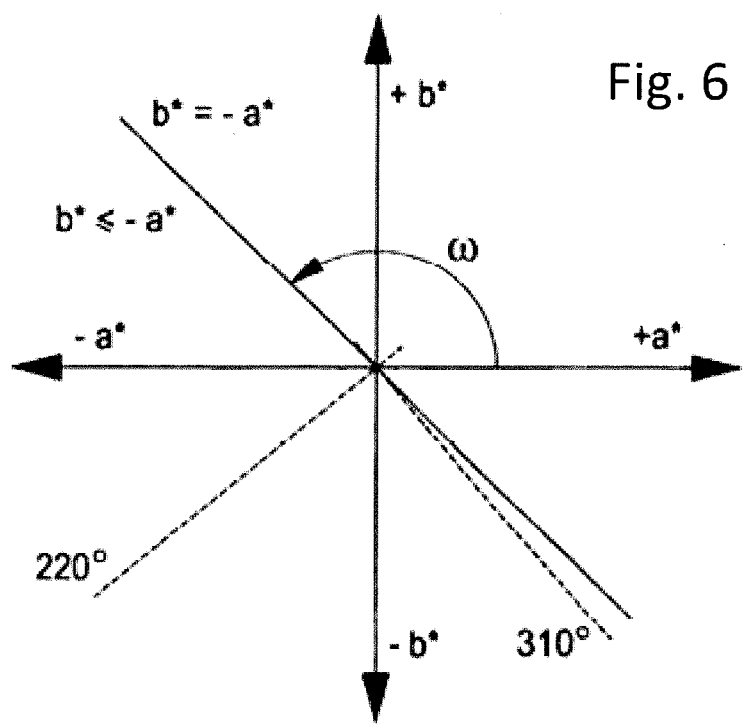
FIG. 6 shows the horizontal plane of the color sphere for L=50.

The CIELAB color space is organized in a spherical form with the L* axis running from top to bottom and the a* and b* axis being placed in an horizontal plane. In general, CIE L* scale values are units of light reflectance measurement, and the higher the value is, the lighter the color is since a lighter colored material reflects more light. The L* scale contains 100 equal units of division, absolute black is at the bottom of the scale (L=0) and absolute white is at the top of the scale (L=100). Thus in measuring L* values of the materials used in the absorbent articles in the context of the present disclosure, the lower the L* scale value, the darker the material. The a* axis is the axis red/green (+a*=red, −a* =green), while b represents the axis yellow/blue (+b*=yellow, −b*=blue). The L*, a* and b* values can be measured using any suitable equipment, for example the colorimeter MINOLTA mode CR-300 instrument (available from the Minolta Company, Japan) which provides the coordinates L*, a*, b* and from which the ΔE* value between two color points can be determined. FIG. 5 shows the color sphere used for the representation of color in the CIELAB system, and FIG. 6 shows the horizontal plane of the color sphere for L=50.

The L*a*b* values of the colored areas can be measured on the material taken in-situ on the carrier layer as such and/or in-situ on body facing side of the finished absorbent product.

As said above, in certain embodiments, it may be that the hue of the color of the lateral zones may be selected in the blue or green region rather than in the yellow or red region for aesthetic purpose. Furthermore, it has been found that blue and green pigmented nonwoven may better be able to hide underlying stains of blood or urines. Thus, the measured a* and b* values may be advantageously such that the relation b* less than or equal to −a* is fulfilled. This relation may also be expressed in term of angles values reported to the horizontal color disc represented on FIG. 6. Taking any color on the +a* axis as having an angle ω ("omega") of 0, any color on the +b* as having an angle ω of +90° and so forth, and in that case the relation b* less than or equal to −a* is equivalent to having an angle ω of from 135° to 315°. In particular embodiments, it was found that colors in the blue or lilac tone, for which an angle ω of from 135° to 315°, or 180°-290° is suitable.

The absorbent product may also include an additional adhesive layer arranged between the liquid inlet layer and the topsheet, and wherein the topsheet is attached to the carrier layer through the liquid inlet openings in the liquid inlet region. Thereby, the liquid inlet layer will be held from two sides, which allows the open area of the liquid inlet region to be larger, so that the slitted liquid inlet material can be extended to a greater degree, which in turn leads to saving liquid inlet material.

The topsheet layer and the backsheet layer of the absorbent product extend together laterally outside of the absorbent core along the whole circumference thereof. The topsheet layer can include any material liquid-permeable known for the purpose, i.e. soft and liquid pervious, such as a layer of nonwoven material or a perforated plastic film, plastic or textile mesh, and fluid permeable foam layers. The top sheet can also include a laminate of two or more sheets of the same or different topsheet material, or where the top sheet layer includes different materials within different parts of the fluid permeable wearer-facing surface. In order for color differences or colored areas to be visible for the user, the liquid permeable topsheet may suitably include a see-through material, through which the colored areas or different color is visible. The combined topsheet material and liquid inlet layer material may have a maximum opacity, which is sufficiently low for the colored areas to be visible through both these layers. A see-through material can be a nonwoven or plastic material, which is sufficiently transparent for the color difference to be visible or at least perceived through the material; or it can be a relatively opaque material comprising apertures through which the color difference is visible, such as an apertured plastic or nonwoven material. The see-through material may also be a textile mesh, having openings between the threads in the material, through which the color difference is visible. It is important that the properties of the topsheet are chosen so that the colored areas present on the carrier layer can be discerned from the body facing side of the absorbent product. Thus, it may be suitable to choose the material for the top sheet such that the opacity of the combined liquid inlet layer material and the topsheet material is sufficiently low for the colored areas to be discerned from the body facing side of the absorbent product. The combined opacity is suitably 5-70%, or 10-70%, or 10-60%.

The liquid-impermeable back sheet layer is arranged on a garment facing surface of the product and is intended to be in contact with the garments during use. Backsheet materials that are only fluid repellant may be used in instances where relatively small amounts of body fluid are expected to be taken up. The back sheet layer can include a liquid-impermeable plastic film, a nonwoven sheet which has been coated with a liquid barrier material in order to be fluid-impermeable, fluid impermeable foams and fluid impermeable laminates, or any other flexible material sheet which has the ability to withstand liquid penetration. However, it can be advantageous if the liquid-impermeable back sheet layer is breathable, i.e. permits the passage of water vapour through the back sheet. Furthermore, the backsheet may have an outer, garment-facing surface of a textile material such as nonwoven.

The absorbent fibrous layer can be made up of absorbent material, such as cellulose fluff pulp, tissue, etc. and may contain superabsorbents, i.e. polymer materials which are able to absorb body fluid corresponding to many times their own weight and form a hydrogel. The superabsorbents may be mixed with cellulose fluff pulp and/or may be arranged in pockets or layers in the absorbent fibrous layer. The fibres may be pulp fibres and the superabsorbent material may be polyacrylate-based particles.

Moreover, the absorbent core can further include non-absorbent components such as stiffening elements, shaping elements, binders, etc. The absorbent core may for example include absorbent material in the form of an embossed layer including cellulose pulp and superabsorbent particles. The absorbent fibrous layer may suitably have a density of 0.092-0.160 g/cm$^3$ and a basis weight 200-640 g/m$^2$. The absorbent core may further incorporate components for improving the properties of the absorbent core, such as binder fibers, fluid-dispersing materials, wetness indicators etc., as known in the art.

When the above absorbent product is in the form of a sanitary napkin, light incontinence guard or the like, it may further include fastening means for fastening of the absorbent product inside a supporting pant garment, such as a pair of underpants. The fastening means may be in the form of two longitudinally extending bands of pressure sensitive adhesive arranged on the garment-facing surface of the backsheet. The fastening means can be covered by a releasable protective layer, e.g. a siliconized paper, a nonwoven or any other releasable material as is known in the art. Before placing the absorbent product in the supporting pant garment, the protective layer is removed from the fastening means to expose the adhesive and make it available for fastening to the pant garment.

The above absorbent product can be manufactured in various ways. When the central liquid inlet region of the absorbent product is obtained by cutting a pattern of slits and extending the liquid inlet layer material transversely, the inlet layer is suitably secured in its extended state, to prevent the dilated openings from returning to a more closed condition. This can be done by means of adhesive attachment, wherein an adhesive is applied to parts of the area of the inlet layer itself or to adjacent components. The most effective attachment is obtained when substantially the entire surface are which is in contact with an adjacent component is covered with adhesive, as a fine pattern or as a layer completely covering the surface. If the liquid inlet material is a perforated non-extended material, the requirements of securing it to adjacent components are lower, but it may still be preferred to secure the layer over its entire surface.

When manufacturing an absorbent product the same materials as described above in relation to the absorbent product can be used.

The above absorbent product can be manufactured by means of the following method. The method includes a step of cutting a plurality of slits in a central region of a continuous web of liquid inlet layer material, so that the slits extend longitudinally in the machine direction. In certain embodiments, the web of liquid inlet layer material is a web of polymer foam having open or closed cells. The slits can be cut in a pattern, and have lengths and distances in relation to each other as described above in relation to the absorbent product. For example, the slits may have a length in the longitudinal direction of 3.0-20.0 mm, or 4.0-16.0 mm, or 5.0-12.0 mm. After having been slitted, the continuous web of liquid inlet layer material is extended transversally in the cross machine direction, whereby the slits are dilated into openings, having dimensions and patterns as described above in relation to the absorbent product. The extension can be done by grabbing the longitudinal side edges of the material and drawing them transversely away from each other. The web of liquid inlet layer material is extended transversally in the cross machine direction until the longitudinally central region has a desired transversal width, thereby dilating the slits into openings. The slitted and extended central region of the continuous web of liquid inlet layer material will form the liquid inlet region in the final absorbent product. When extending the web of liquid inlet material transversally in the cross machine direction, the web of liquid inlet material is extended to a predetermined desired transversal width, thereby dilating the slits into openings. One or more colored area is present on the web of carrier material before applying adhesive thereto. The colored areas can be applied to the web of carrier material by printing, in a printing step comprised in the method of manufacturing the absorbent product, or a pre-printed carrier material can be provided. Other means of applying colored areas may also be conceivable.

In addition to the colored areas provided on the carrier layer, additional colored areas can be provided on a surface of the topsheet. Similarly, such additional areas may be applied to the topsheet material in a printing step comprised in the method of manufacturing the absorbent product, or a pre-printed topsheet material can be provided.

An adhesive is applied to a continuous web of carrier material, and the web of carrier material is combined with the continuous web of liquid inlet layer material into a combined web, which is subsequently cut into inlet layer components. The adhesive can be applied to the carrier material by spraying or application by means of slot nozzle equipment. Absorbent fibrous material is provided in the form of discrete absorbent fibrous components, which are combined with the inlet foam layer component and enclosed between a continuous web of topsheet material and a continuous web of backsheet material. At least the topsheet material and the backsheet material are joined along the outer edges of the absorbent product. The resulting combined material is cut into a desired shape, thus obtaining the absorbent product. The absorbent fibrous components can be obtained can be obtained in any other suitable way, such as by cutting pieces of a desired shape from a continuous web of fibrous absorbent material, or by mat formation.

In order to increase material saving, the web of liquid inlet layer material may be transversally extended until the longitudinally central region has a transversal width which is equal to the transversal minimum width of the absorbent core component. The web of liquid inlet layer material may be extended to the same degree over its whole longitudinal length, in order to facilitate the extension step.

The method may also include a step of applying adhesive to the surface of the web of topsheet material facing the liquid inlet layer component before enclosing the core components, and pressing the layers together so that the topsheet material layer attaches to the carrier layer through the openings formed in the liquid inlet layer.

Description of the Drawings

FIGS. 1-4 schematically illustrate the above described absorbent product and method by way of example.

Figure 2A:
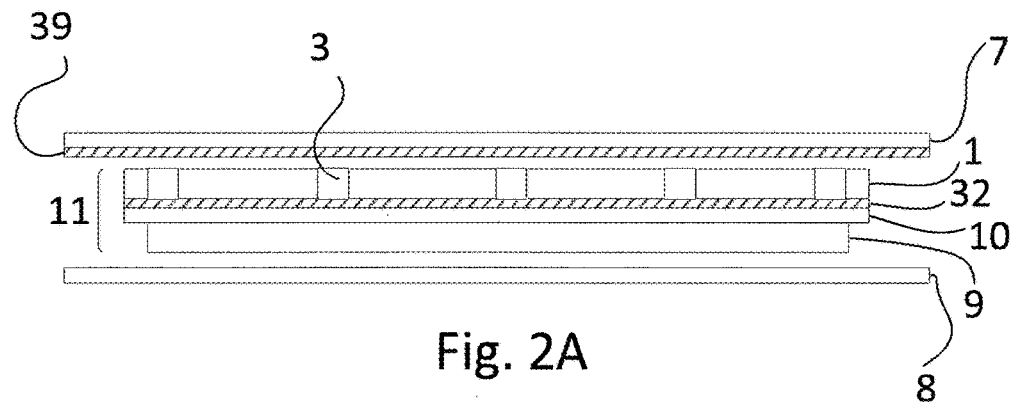
FIG. 2A shows a schematic cross-sectional view of the product of FIG. 1 across the line A-A in FIG. 1.

FIG. 1A shows top view of an absorbent product in the form of sanitary napkin having a longitudinal direction L and a transversal direction T, and FIG. 2A shows a cross section of the same product along the line A-A. The sanitary napkin of FIG. 1A is depicted with wings, which can as well be omitted. The absorbent product includes a liquid permeable topsheet 7, a liquid impermeable backsheet 8, and an absorbent core 11 enclosed between the topsheet 7 and the backsheet 8. The absorbent core 11 has a length L1 extending in a longitudinal direction of the absorbent product, between a front edge 13 and a rear edge 14 of the absorbent core, and it has substantially longitudinally extending side edges 24, 25. As can be seen in FIGS. 1A and 2, the topsheet 7 and backsheet 8 extend outside of the circumference of the absorbent core 11. In the shown example, the absorbent core 11 includes a front part having front maximum transversal width M1, and a rear part having a rear maximum transversal width M2, and the absorbent core 11 further has an intermediate minimum transversal width M3 at a point located longitudinally between said front part and said rear part, where the absorbent core is narrower at the intermediate minimum transversal width M3 than at the front and rear maximum transversal widths M1, M2. The absorbent core 11 includes a front end portion 15, a rear end portion 17, and an intermediate portion 16, located between the front and rear portions 15, 17 in the longitudinal direction of the absorbent core 11. The front and rear end regions 15, 17 each have a length L2, L3 in the longitudinal direction L from the front end edge 13 and the rear edge 14.

In this embodiment, the absorbent core 11 includes an intermediate portion 16 located between the front portion 15 and the rear portion 17 in the longitudinal direction of the absorbent core 11, and the intermediate minimum transversal width M3 is located within the intermediate portion 16.

Colored areas 21, 22 are present on the carrier layer 10 in the front and rear end regions 15, 17 of the absorbent core 11, and a colored area 20 is present in the intermediate portion 16 of the absorbent core 11. By means of a liquid inlet foam material 101 having an opacity of 5-60%, or 10-50%, or 10-40% and suitably also a liquid permeable topsheet 7 in the form of a see-through material, through which the colored areas 20, 21, 22 are visible. FIG. 1A shows how the colored areas 20, 21, 22 appear with two different color intensities.

Figure 1B:
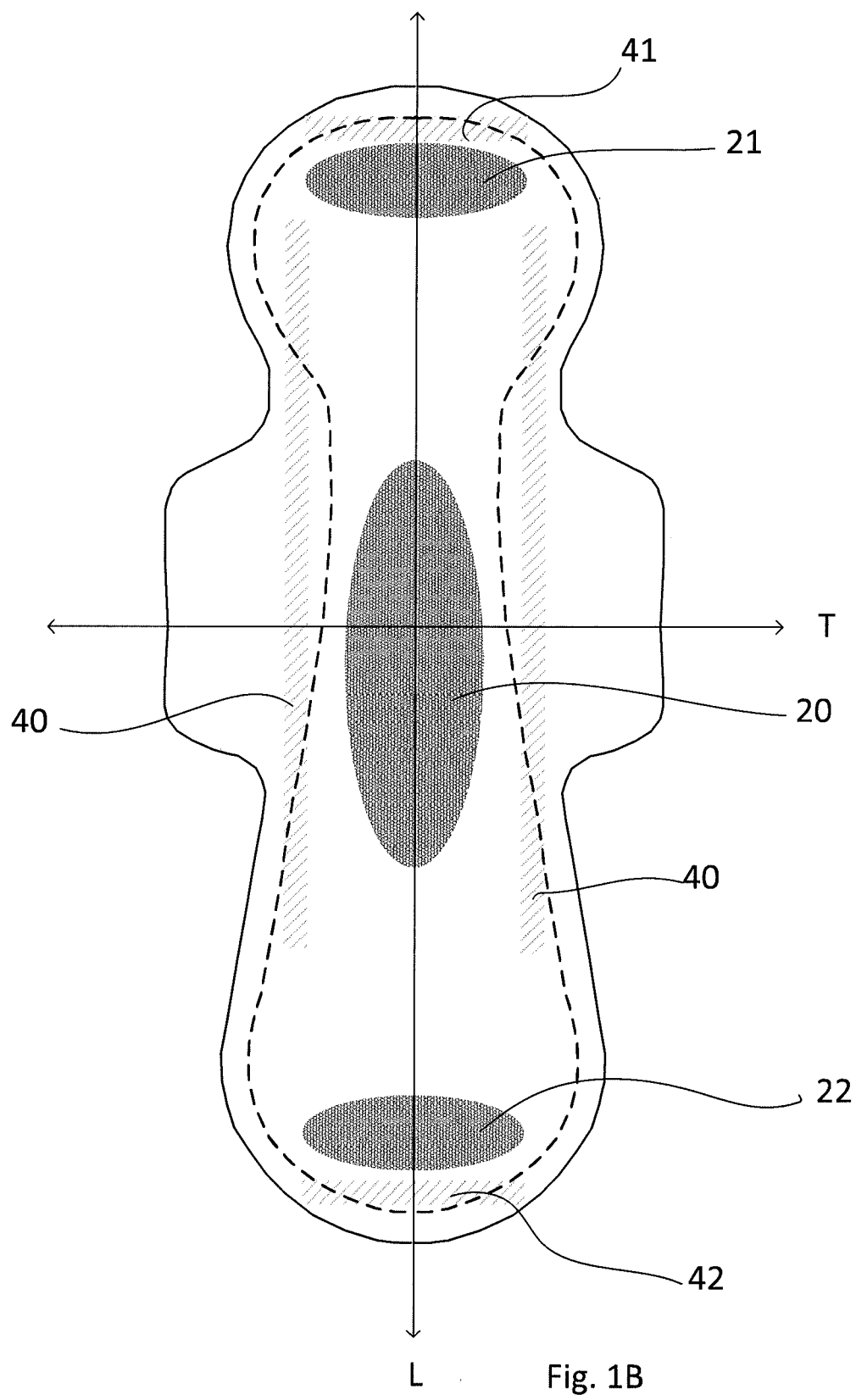
FIG. 1B is a schematic top view of a similar product as the one shown in FIG. 1A, illustrating how colored areas can be located in the product.

FIG. 1B is a schematic top view of a product similar to the one shown in FIG. 1A, illustrating how colored areas can be located in the product. In this case the colored areas 20, 21, 22 are provided on the carrier layer, and additional colored areas 40, 41, 42 are provided on the topsheet. For simplicity reasons, only the colored areas are shown in FIG. 1B, and the contour of the absorbent core 11 is indicated by a dashed line.

FIG. 2A is a schematic cross-sectional view of the product of FIG. 1 across the line A-A in FIG. 1. The colored areas 20, 21, 22 provided on the carrier layer, and the additional colored areas 40, 41, 42 provided on the topsheet are not shown in FIG. 2A. As shown in FIG. 2A, the absorbent core 11 includes an absorbent fibrous layer 9 arranged on the side of the absorbent core, which is closest to the liquid impermeable backsheet 8, a liquid inlet layer 1 arranged on the side of the absorbent core, which is closest to the liquid permeable topsheet 7. FIG. 1A shows how the absorbent core 11 comprises a transversally central liquid inlet region 23, which extends in the longitudinal direction of the absorbent core and have substantially longitudinally extending side edges 26, 27, but the distance between these side edges can vary slightly. The liquid inlet region 23 has a transversal width M4, which is equal to the minimum transversal width M3 of the absorbent fibrous layer 9, so that side edge regions 5, 6 are arranged in the front and rear portions 15, 17 transversally outside of the liquid inlet region 23. In this example, the side edges 16, 27 of the central liquid inlet region 23 are parallel to each other and to the longitudinal axis of the absorbent product, so that the width M4 is the same over its entire length. The side edge regions 5', 6' of the front portion 15 have a maximum width M6, and the side edge regions 5", 6" of the rear portion 17 have a maximum width M5. In the shown example, the width M6 of the front side edge regions 5', 6' is the same as the width M5 of the rear side edge regions 5", 6", but the front side edge region width M6 may also be smaller than the rear side edge region width M5.

Figure 2B:
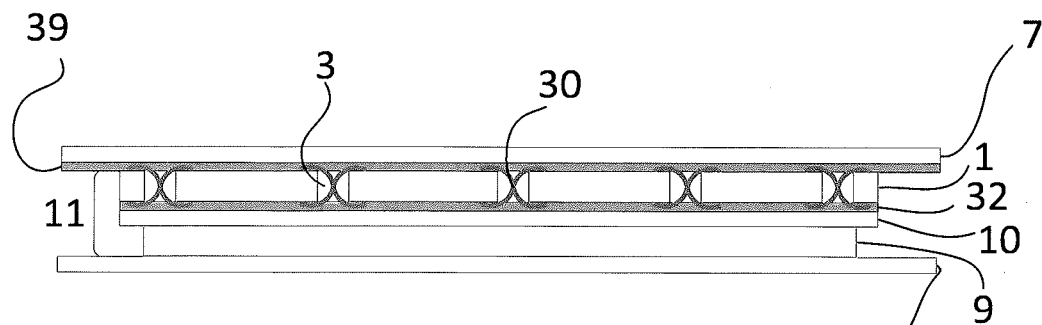
FIG. 2B shows in a schematic cross-sectional view schematically how the topsheet and the carrier layer are attached to each other through the openings in the liquid inlet layer along the line A-A in FIG. 1.

The absorbent product includes a carrier layer 10 arranged between the liquid inlet layer 1 and the absorbent fibrous layer 9, and an adhesive layer 32 arranged between the liquid inlet layer 1, and the carrier layer 10. Further, an additional adhesive 39 layer can be arranged between the liquid inlet layer 1 and the topsheet 7, and the topsheet 7 can be attached to the carrier layer 10 through the dilated slit openings 3 by letting the adhesive layers 32, 39 join through the dilated slit openings 3, which is illustrated in FIG. 2B at the point 30. When the layers of the absorbent product are combined, the carrier layer 10 will adhesively attach to the topsheet layer 7 through the openings 3 in the liquid inlet region 23, by means of the adhesive layers 39, 32.

The liquid inlet layer is free from liquid inlet openings in the side edge regions 5, 6. In the shown example, the transversal width M4 of the liquid inlet region 23 is equal to the minimum transversal width M3 of the absorbent core, which means that no side edge regions are present at this location. However, if desired side edge regions may be present transversally outside of the central portion along the entire length of the absorbent core.

The plurality of inlet openings 3 provided in the liquid inlet layer 1 can be formed from a plurality of slits, which have been dilated into openings by transversally extending a web of liquid inlet foam material, from which the liquid inlet layer 1 is made, before incorporation into the product. This is shown in more detail in FIGS. 3A and 3B. In this example, the liquid inlet region 23 extends longitudinally along 100% of the absorbent core 11.

Figure 3A:
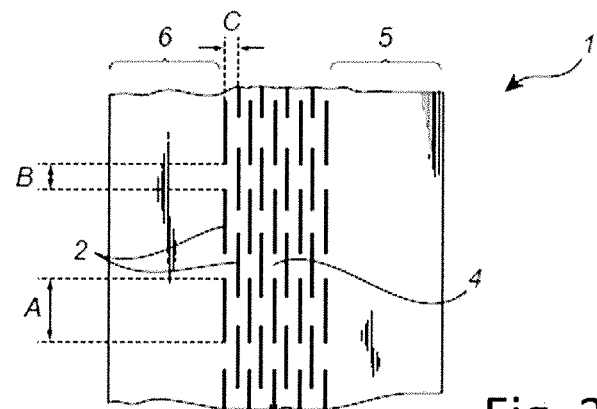
FIG. 3A shows a schematic top view of a liquid inlet foam material before it has been extended.

FIG. 3A shows a top view of a liquid inlet foam material 1 after it has been slitted but before it has been extended, and shows how a pattern of longitudinal slits 2 has been cut. The yet non-extended liquid inlet foam material 1 has in its transversal direction a central region 4 with slits and two side edge regions 5, 6 without slits. The slits 2 in FIG. 3A are straight, but may have any suitable shape such as for example wave-shaped. In the shown example, the slits 2 are provided in a pattern with staggered rows extending in the longitudinal direction of the inlet material 1. The slits 2 are located at a distance B within one longitudinal row, and adjacent rows are arranged at a distance C from each other in the transversal direction. Each slit 2 in the pattern has a slit length A and a width W1.

Figure 3B:
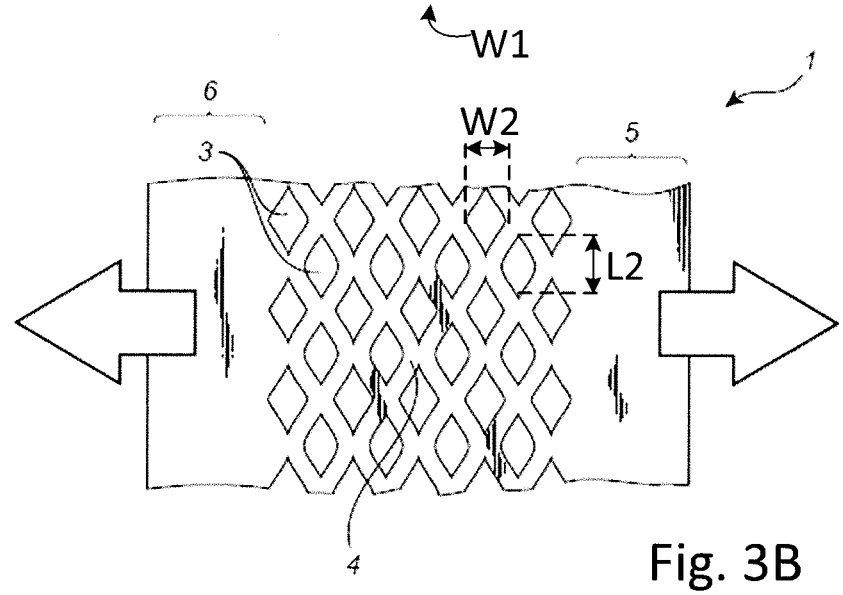
FIG. 3B shows a schematic top view the liquid inlet foam material of FIG. 3A after it has been extended, i.e. after the slits have been dilated to form openings.

FIG. 3B the liquid inlet foam material of FIG. 3A after it has been extended in the direction transversal to the slit 2 direction, i.e. after the slits 2 have been opened to form openings 3. The slits 2 have now been dilated to diamond shaped openings, or diamond pockets, and have a longitudinal length L2 and a transversal width W2. The side edge regions 5, 6 are still free from openings.

In the shown example, the part of the central region 4 forming the liquid inlet region 23 has a transversal width M4, which is equal to the minimum transversal width M3 of the absorbent fibrous layer 9, so that side edge regions 5, 6 are arranged in the front and rear portions 15, 17 transversally outside of the liquid inlet region 23. In this example, the side edges 16, 27 of the central liquid inlet region 23 are parallel to each other and to the longitudinal axis of the absorbent product, so that the width M4 is the same over its entire length. The side edge regions 5', 6' of the front portion 15 have a maximum width M6, and the side edge regions 5", 6" of the rear portion 17 have a maximum width M5. In the shown example, the width M6 of the front side edge regions 5', 6' is the same as the width M5 of the rear side edge regions 5", 6", but the front side edge region width M6 may also be smaller than the rear side edge region width M5.

Figure 4:
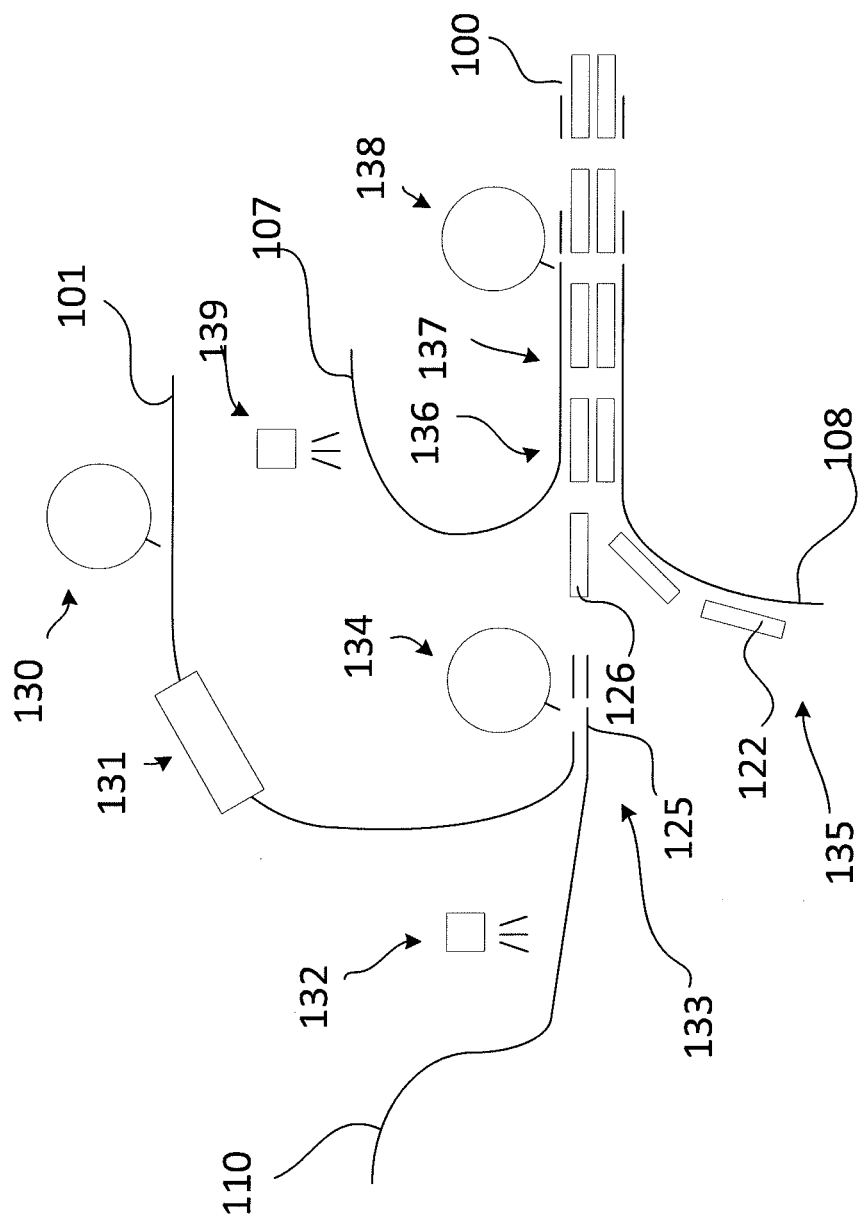
FIG. 4 shows schematically a method of manufacturing an absorbent product including an extended liquid inlet layer.

FIG. 4 shows schematically a method of manufacturing an absorbent product, including the steps of
- cutting 130 a plurality of slits 2 in a central region 4 of a continuous web of liquid inlet foam material 101, said slits extending longitudinally in the machine direction;
- extending 131 the web of liquid inlet foam material 101 transversally in the cross machine direction to a predetermined desired transversal width M4, whereby the slits 2 are dilated into openings 3;
- applying adhesive 132 to a continuous web of carrier material 110, where one or more colored areas 20, 21, 22 are present on the web of carrier material 110 before applying adhesive thereto;
- combining 133 the continuous web of liquid inlet foam material 101 and the web of carrier material 110 into a combined web 125;
- cutting 134 inlet foam layer components 126 from the combined web 125;
- providing 135 discrete absorbent components 122;
- enclosing 136 the inlet foam layer component 126 and absorbent component 122 between a continuous web of topsheet material 107 and a continuous web of backsheet material 108;
- joining 137 at least the topsheet material 107 and the backsheet material 108 along the outer edges of the absorbent product; and
- cutting 138 the combined material into a desired shape, thus obtaining the absorbent product 100.

The method shown in FIG. 4 also includes applying adhesive 139 to the surface of the web of topsheet material 107 facing the liquid inlet foam component 126 before enclosing the core components 126, 122, and pressing the layers together 135 so that the topsheet material layer 107 attaches to the carrier layer 110 through the openings 3 formed in the liquid inlet layer 101. The colored areas 20, 21, 22 can be applied to the web of carrier material 110 by printing. The method may further include applying one or more colored areas 40, 41, 42 on a surface of the topsheet 7 by printing.

EXAMPLES

The thickness of a material layer suitable for the liquid inlet layer is measured with an applied pressure of 0.5 kPa on a non-apertured and non-stretched piece of material. The thickness gauge foot suitably measures 45×45 mm, or in any way it must be smaller than the sample. Carefully separate the liquid inlet layer from the article, and measure thickness on a representative area. Lower the foot slowly and gently over the sample, and let it rest for 10 seconds before reading the thickness. In case the foam has an irregular thickness, an average value should be taken from five representative measurement spots.

Density is calculated by weighing the sample (in grams), and then dividing the weight by the sample volume (in cm$^3$). Volume is measured by multiplying the thickness (measured as above) by the sample area. The density refers to homogenous material, thus excluding any slits or openings.

Opacity is measured according to International Standard ISO 2471:2008(E)—Paper and board—Determination of opacity (paper backing)—Diffuse reflectance method. The method originates from the paper industry, but it is suitable also in this context. Carefully separate the inlet layer from the absorbent product. Measure opacity on an area that is free from slits or apertures. In case the opacity varies over the area of the inlet layer, e.g. due to partial coloration or differences in basis weight, the least opaque area should be considered representative for the inlet layer.

Table 1 below shows examples of suitable commercially available materials that can be used for the liquid inlet layer of the absorbent core. The reference sample is an airlaid nonwoven. An air laid nonwoven can be produced with fluff, wood pulp, where the fluff fibers are dispersed into a fast mowing air stream and condensed onto a moving screen by means of pressure and vacuum. The web can be bonded with resin and/or thermal plastic resin dispersed within the pulp. The web can be thermobonded (by heat), latex bonded (with adhesive) or multibonded (a combination of thermo and latex bonding) or mechanically bonded (high compression and temperature, bonding by hydrogen).

TABLE 1

Measurements on foam and wadding materials

| | Material designation | Material type | Thickness (mm) | Basis Weight (g/m$^2$) | Density (kg/m$^3$) | Opacity, (%) ISO 2471* |
|---|---|---|---|---|---|---|
| 1 | Recticel Bulfast 35H | Polyurethane foam | 1.96 | 66.9 | 34.1 | 35 |
| 2 | Recticel T23/20 | polyurethane foam | 2.54 | 55.0 | 21.7 | 32 |
| 3 | Recticel T25090 | polyurethane foam | 2.37 | 55.2 | 23.3 | 34 |
| 4 | Recticel T46090 | polyurethane foam | 3.11 | 126.5 | 40.7 | 42 |
| 5 | FXI CAZ080A | polyurethane foam | 1.81 | 57.9 | 32.0 | 53 |
| 6 | Berry Airten B5 | High loft NW | 1.06 | 50 | 47.2 | 28 |
| 7 | Berry Airten B8 | High loft NW PET Bico coPET/PET, Bico PP/PET | 1.27 | 50 | 39.4 | 30 |
| 8 | Berry Airten 50 MFU | Dual layer NW PET/BiCo PP/PE | 1.30 | 50 | 38.5 | 46 |
| 9 | Jacob Holm | Spunlace NW Material code: 61.050.0110; 40% Viscose, 60% Synthetic fibers | 0.60 | 50 | 83.3 | 46 |
| 10 | Suominen 2B | Spunlace NW Material code 137113-2B; 70% Polyester, 30% Bico | 1.00 | 65 | 65.0 | 34 |
| 11 | Suominen 3 | Spunlace NW Material code 137108-3; 30% Viscose, 70% Polyester | 1.00 | 55 | 55.0 | 40 |
| 12 | TWE 40 gsm | High loft NW ParaTherm Loft 349/40; PET | 1.55 | 40 | 25.8 | 20 |
| 13 | TWE 55 gsm | High loft NW ParaTherm Loft 142/60; PP/PE/PET. | 2.60 | 55 | 23.1 | 32 |
| ref | SCA Airlaid 70NL81 | Cellulose fibres bonded with latex and bico fibres. | 1.10 | 70 | 63.6 | 64 |

*ISO 2471: 2008 (E) - Paper and board - Determination of opacity (paper backing) - Diffuse reflectance method A liquid inlet foam material having low thickness and density is preferred for reasons of comfort and discretion.

The material of sample 5 is a foam having high reflection due to inclusion of white pigment. The foam of sample 4 has relatively high thickness and basis weight, which gives a higher opacity. The material of sample 2 is a foam having the most preferred opacity, although all foams in the table are transparent enough to be suitable for the liquid inlet layer. All wadding samples 6-13 have low opacity as compared to the reference.

The invention claimed is:

1. An absorbent product comprising:
   a liquid permeable topsheet;
   a liquid impermeable backsheet;
   an absorbent core enclosed between the topsheet and the backsheet, said absorbent core having a length extending in a longitudinal direction of the absorbent product, between an absorbent core front edge and an absorbent core rear edge, and having longitudinally extending absorbent core side edges, and comprising:
      an absorbent fibrous layer arranged on the side of the absorbent core, which is closest to the liquid impermeable backsheet;
      a liquid inlet layer arranged on the side of the absorbent core, which is closest to the liquid permeable topsheet, said liquid inlet layer comprising a transversally central liquid inlet region extending in the longitudinal direction of the absorbent core and substantially longitudinally extending liquid inlet layer side edges, wherein the central liquid inlet region is covered by a plurality of inlet openings arranged in a pattern; and
      a carrier layer arranged between the liquid inlet layer and the absorbent fibrous layer, said carrier layer comprising one or more colored areas located below the central liquid inlet region,
   wherein the liquid inlet layer is made of a material having an opacity of 5-60%, so that the one or more colored areas are visible through the material of the liquid inlet layer, and
   wherein the liquid permeable topsheet comprises a see-through material, through which the one or more colored areas are visible.

2. The absorbent product of claim 1, wherein the plurality of inlet openings in the liquid inlet layer are formed from a plurality of slits, which have been dilated into inlet openings by transversally extending a web of liquid inlet material, from which the liquid inlet layer is made, before incorporation into the product.

3. The absorbent product of claim 1, wherein the one or more colored areas are located on a surface of the carrier layer facing the liquid inlet layer or on a surface facing the absorbent fibrous layer.

4. The absorbent product of claim 1, wherein said absorbent core comprises an absorbent core front portion and an absorbent core rear portion and an absorbent core intermediate portion located between the absorbent core front and rear portions in the longitudinal direction of the absorbent core, and wherein the one or more colored areas of the carrier layer are located in one, two or all of said portions.

5. The absorbent product of claim 1, wherein said central liquid inlet region extends along the entire longitudinal length of the absorbent core.

6. The absorbent product of claim 1, wherein the liquid inlet layer comprises liquid inlet layer side edge regions located on either side of the central liquid inlet region in a transversal direction of the absorbent product, between the central liquid inlet region and the longitudinally extending liquid inlet side edges of the absorbent core, and wherein the liquid inlet material in each of said liquid inlet layer side edge regions is free from openings.

7. The absorbent product of claim 5, wherein the one or more colored areas are located on a surface of the carrier layer below said liquid inlet layer side edge regions.

8. The absorbent product of claim 1, wherein the one or more colored areas are applied to the carrier layer by printing.

9. The absorbent product of claim 1, wherein the liquid inlet layer is made of a liquid inlet polymer foam material or wadding material having a thickness of 0.5-3 mm.

10. The absorbent product of claim 1, wherein the material making up the liquid inlet layer is a hydrophobic polymer foam material having open or closed cells.

11. The absorbent product of claim 1, wherein one or more additional colored areas are printed on a surface of the topsheet.

12. The absorbent product of claim 1, wherein the one or more colored areas on the carrier layer have different colors or different color intensity.

13. The absorbent product of claim 11, wherein the one or more additional colored areas on the topsheet have different colors or different color intensity.

14. The absorbent product of claim 1, wherein the carrier layer is made of a nonwoven material or tissue material, or a combination thereof.

15. A method of manufacturing an absorbent product, comprising:
   cutting a plurality of slits in a central region of a continuous web of liquid inlet material, said slits extending longitudinally in the machine direction;
   extending the web of liquid inlet layer material transversally in the cross machine direction a predetermined desired transversal width, thereby dilating the slits into openings;
   applying adhesive to a continuous web of carrier material having one or more colored areas;
   combining the continuous web of liquid inlet layer material and the web of carrier material into a combined web;
   cutting liquid inlet layer components from the combined web;
   providing absorbent components from a continuous web of fibrous absorbent material;
   enclosing the liquid inlet layer component and the absorbent component between a continuous web of topsheet material and a continuous web of backsheet material;
   joining at least the topsheet material and the backsheet material along the outer edges; and
   cutting the combined material into a desired shape, thus obtaining an absorbent product,
   wherein the liquid inlet layer material has an opacity of 5-60%, so that the one or more colored areas are visible through the liquid inlet layer material, and
   wherein the topsheet material comprises a see-through material, through which the one or more colored areas are visible.

16. The method of claim 15, wherein said one or more colored areas are applied to the web of carrier material by printing.

17. The method of claim 15, further comprising applying one or more colored areas on a surface of the topsheet.

18. The method of claim 15, wherein said web of liquid inlet material is a web of polymer foam having open or closed cells.

* * * * *